United States Patent [19]

Sirrenberg et al.

[11] Patent Number: 4,552,900
[45] Date of Patent: Nov. 12, 1985

[54] 3-(PYRIMIDIN-5-YL-OXYPHENYL)-1-BENZOYL-(THIO)-UREA COMPOUNDS USEFUL AS PESTICIDES

[75] Inventors: Wilhelm Sirrenberg, Sprockhoevel; Fritz Maurer, Wuppertal; Erich Klauke, Odenthal; Benedikt Becker, Mettmann; Wilhelm Stendel, Wuppertal, all of Fed. Rep. of Germany

[73] Assignee: Bayer Aktiengesellschaft, Leverkusen, Fed. Rep. of Germany

[21] Appl. No.: 589,986

[22] Filed: Mar. 15, 1984

[30] Foreign Application Priority Data

Mar. 30, 1983 [DE] Fed. Rep. of Germany ....... 3311703

[51] Int. Cl.⁴ .................. A61K 31/505; C07D 239/02
[52] U.S. Cl. ................................. 514/269; 514/274; 544/298; 544/318
[58] Field of Search .............. 544/298, 318; 424/251; 514/269, 274

[56] References Cited

U.S. PATENT DOCUMENTS 3,748,356 7/1973 Wellinga ............................ 424/251
4,166,124 8/1979 Wellinga ............................ 424/251

Primary Examiner—Donald G. Daus
Assistant Examiner—Cecilia Shen
Attorney, Agent, or Firm—Sprung, Horn, Kramer & Woods

[57] ABSTRACT 3-(Pyrimidin-5-yl-oxy-phenyl)-1-benzoyl-(thio)-ureas of the formula

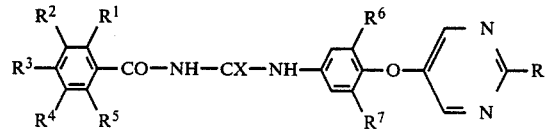

in which
R represents hydrogen, alkyl, cycloalkyl, halogenoalkyl or optionally substituted aryl,
$R^1$ represents hydrogen, nitro, halogen, alkyl or alkylthio,
$R^2$, $R^3$, $R^4$ and $R^5$ are indentical or different and represent hydrogen or halogen,
$R^6$ and $R^7$ are identical or different and represent hydrogen, halogen or alkyl and
X represents oxygen or sulphur
which possess arthropodicidal activity. Novel intermediates are also shown.

12 Claims, No Drawings

3-(PYRIMIDIN-5-YL-OXYPHENYL)-1-BENZOYL-(THIO)-UREA COMPOUNDS USEFUL AS PESTICIDES

The invention relates to new 3-(pyrimidin-5-yl-oxyphenyl)-1-benzoyl-(thio)ureas, processes for their preparation and their use as pest-combating agents, in particular as arthropodicides, e.g. insecticides.

It is already known that certain benzoylureas, such as, for example, 1-(2,6-difluorobenzoyl)-3-(4-chlorophenyl)-urea, possess insecticidal properties (see, for example, DE-AS (German Published Specification) No. 2,123,236).

The new 3-(pyrimidin-5-yl-oxy-phenyl)-1-benzoyl-(thio)ureas of the formula (I) have been found,

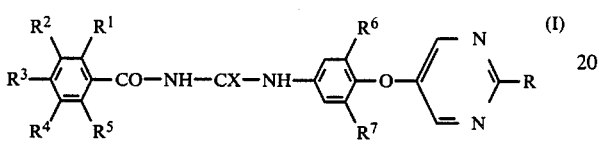

in which
R represents hydrogen, alkyl, cycloalkyl, halogenoalkyl or optionally substituted aryl,
$R^1$ represents hydrogen, nitro, halogen, alkyl or alkylthio,
$R^2$, $R^3$, $R^4$ and $R^5$ are identical or different and represent hydrogen or halogen,
$R^6$ and $R^7$ are identical or different and represent hydrogen, halogen or alkyl and
X represents oxygen or sulphur.

These new compounds possess powerful biological, in particular insecticidal, properties which make it possible to use them as pest-combating agents, in particular as insecticides.

Furthermore, it has been found that the new 3-(pyrimidin-5-yl-oxy-phenyl)-1-benzoyl-(thio)ureas of the formula (I) are obtained by a process in which (a) new substituted anilines of the formula (II)

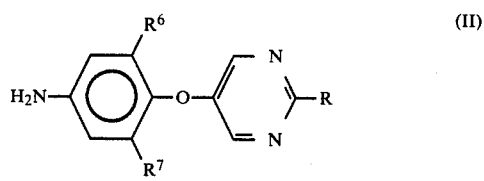

in which R, $R^6$ and $R^7$ have the meanings given above, are reacted with benzoyl iso(thio)cyanates of the formula (III)

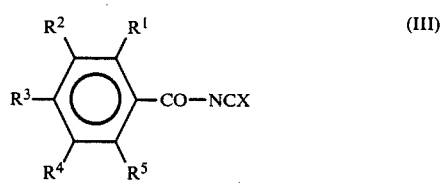

in which X, $R^1$, $R^2$, $R^3$, $R^4$ and $R^5$ have the meanings given above, if appropriate in the presence of a diluent, or (b) pyrimidinyloxy-phenyl iso(thio)cyanates of the formula (IV)

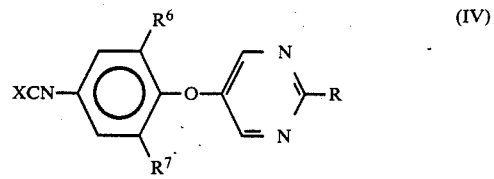

in which X, R, $R^6$ and $R^7$ have the meanings given above, are reacted with benzoic acid amides of the formula (V)

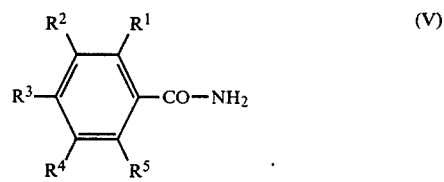

in which $R^1$, $R^2$, $R^3$, $R^4$ and $R^5$ have the meanings given above,
if appropriate in the presence of a catalyst and, if appropriate, in the presence of a diluent.

Alkyl R, $R^1$, $R^6$ and $R^7$ represents straight-chain or branched alkyl having 1 to 12, preferably 1 to 6, in particular 1 to 4, carbon atoms. Methyl, ethyl, n-propyl, iso-propyl, n-butyl, iso-butyl, sec.-butyl and tert.-butyl may be mentioned as examples.

Alkylthio $R^1$ represents straight-chain or branched alkylthio having preferably 1 to 6, in particular 1 to 4, carbon atoms. Methylthio, ethylthio, n-propylthio, iso-propylthio, n-butylthio, iso-butylthio, sec.-butylthio and tert.-butylthio may be mentioned as examples.

Cycloalkyl R represents cycloalkyl having preferably 3 to 8, in particular 3 to 6, carbon atoms. Cyclopropyl, cyclobutyl, cyclopentyl and cyclohexyl may be mentioned as examples.

Halogenoalkyl R represents halogenoalkyl having preferably 1 to 6, in particular 1 to 3, carbon atoms and preferably 1 to 5, in particular 1 to 3, halogen atoms, the halogen atoms being identical or different and preferred halogen atoms being fluorine, chlorine, bromine and/or iodine, in particular fluorine, chlorine and/or bromine, such as trifluoromethyl, trichloromethyl, chlorodifluoromethyl, dichlorofluoromethyl, trifluoroethyl, trichloroethyl, chlorodifluoroethyl, dichlorofluoroethyl and n-pentafluoropropyl.

Optionally substituted aryl R preferably contains 6 or 10 carbon atoms in the aryl part, and phenyl and naphthyl, preferably phenyl, may be mentioned.

Halogen denotes (where not stated otherwise) fluorine, chlorine, bromine and iodine, preferably fluorine, chlorine or bromine.

The aryl radical R can be monosubstituted or polysubstituted by identical or different substituents. Preferred substituents are: halogen, the halogen atoms being identical or different and preferred halogen atoms being fluorine, chlorine or bromine, in particular fluorine or chlorine; alkyl, alkoxy, alkylthio having preferably 1 to 4 carbon atoms, halogenoalkyl, halogenoalkoxy and halogenoalkylthio having preferably 1 to 4, in particular 1 to 3, carbon atoms in the alkyl part and preferably 1 to 5, in particular 1 to 3, halogen atoms, the halogen atoms being identical or different and preferred halogen atoms being fluorine, chlorine, bromine or iodine, in particular fluorine, chlorine or bromine, such as trifluoromethyl, trifluoromethoxy or trifluoromethylthio.

The new compounds of the formula (I) have properties which make it possible to use them as pest-combating agents; in particular, they are distinguished by an excellent insecticidal activity.

The invention preferably relates to new compounds of the formula (I), in which
R represents hydrogen, $C_1$–$C_6$-alkyl, $C_3$–$C_6$-cycloalkyl, halogeno-$C_1$–$C_6$-alkyl or a phenyl radical which is optionally substituted by halogen, $C_1$–$C_4$-alkyl, $C_1$–$C_4$-alkoxy, $C_1$–$C_4$-alkylthio, halogeno-$C_1$–$C_4$-alkyl, halogeno-$C_1$–$C_4$-alkoxy and/or halogeno-$C_1$–$C_4$-alkylthio,
$R^1$ represents hydrogen, nitro, halogen, $C_1$–$C_4$-alkyl or $C_1$–$C_4$-alkylthio,
$R^2$, $R^3$, $R^4$ and $R^5$ are identical or different and represent hydrogen or halogen,
$R^6$ and $R^7$ are identical or different and represent hydrogen, halogen or $C_1$–$C_4$-alkyl and
X represents oxygen or sulphur,
and halogen in each case represents fluorine, chlorine, bromine and/or iodine, preferably fluorine, chlorine or bromine.

Particularly preferably
R represents hydrogen, $C_1$–$C_4$-alkyl, $C_3$–$C_6$-cycloalkyl, halogeno-$C_1$–$C_4$-alkyl, or phenyl which is optionally monosubstituted or polysubstituted by $C_1$–$C_2$-alkyl, $C_1$–$C_2$-alkoxy, $C_1$–$C_2$-alkylthio, halogeno-$C_1$–$C_2$-alkyl, halogeno-$C_1$–$C_2$-alkoxy, halogeno-$C_1$–$C_2$-alkylthio, fluorine, chlorine and/or bromine,
$R^1$ represents hydrogen, fluorine, chlorine, bromine, iodine, nitro, $C_1$–$C_4$-alkyl or $C_1$–$C_4$-alkylthio,
$R^2$, $R^3$, $R^4$ and $R^5$ are identical or different and represent hydrogen, fluorine, chlorine or bromine,
$R^6$ and $R^7$ are identical or different and represent hydrogen, fluorine, chlorine, bromine or $C_1$–$C_4$-alkyl and
X represents oxygen or sulphur.

Very particularly preferred compounds are those of the formula (I), in which
R represents hydrogen, methyl, ethyl, n-propyl, i-propyl, n-butyl, sec.-butyl, i-butyl, tert.-butyl, cyclopropyl, cyclohexyl, or phenyl which is optionally monosubstituted to trisubstituted by methyl, ethyl, trifluoromethyl, trifluoromethoxy, trifluoromethylthio, fluorine, chlorine and/or bromine,
$R^1$ represents fluorine, chlorine, bromine or iodine,
$R^2$, $R^3$, $R^4$ and $R^5$ are identical or different and represent hydrogen, fluorine, chlorine or bromine,
$R^6$ and $R^7$ are identical or different and represent hydrogen, chlorine or methyl and
X represents oxygen or sulphur.

If 3,5-dichloro-4-(2-methyl-pyrimidin-5-yl-oxy)aniline and 2,6-difluoro-benzoyl isocyanate are used as starting materials according to process variant (a), the course of the reaction can be represented by the following equation:

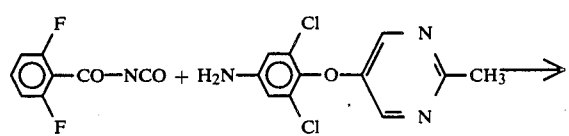

-continued

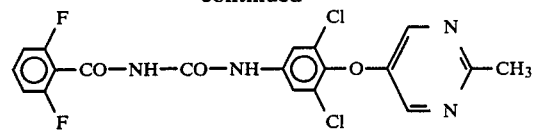

If 3,5-dichloro-4-(2-cyclopropyl-pyrimidin-5-yl-oxy)-phenyl isocyanate and 2-bromo-benzamide are used as starting materials according to process variant (b), the course of the reaction can be represented by the following equation:

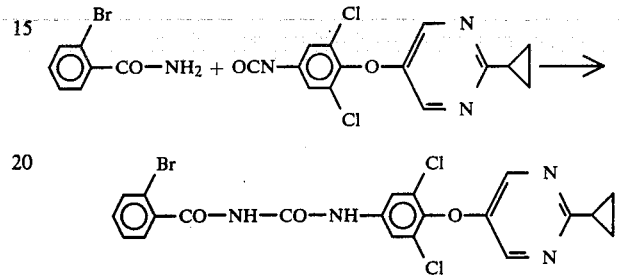

The following may be mentioned as examples of the compounds of the formula (II):

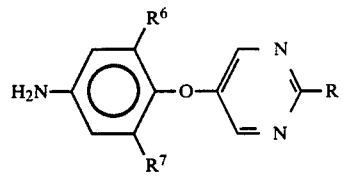

TABLE 1

| $R^6$ | $R^7$ | R | $R^6$ | $R^7$ | R |
|---|---|---|---|---|---|
| H | H | H | H | H | –⌬ |
| H | Cl | H | H | Cl | –⌬ |
| H | CH$_3$ | H | H | CH$_3$ | –⌬ |
| Cl | Cl | H | Cl | Cl | –⌬ |
| Cl | CH$_3$ | H | Cl | CH$_3$ | –⌬ |
| CH$_3$ | CH$_3$ | H | CH$_3$ | CH$_3$ | –⌬ |
| H | H | CH$_3$ | H | H | –⌬–CH$_3$ |
| H | H | tert. C$_4$H$_9$ | | | |
| H | Cl | tert. C$_4$H$_9$ | | | |
| H | Cl | CH$_3$ | Cl | Cl | ◁ |
| H | CH$_3$ | CH$_3$ | | | |

TABLE 1-continued

| R⁶ | R⁷ | R | R⁶ | R⁷ | R |
|---|---|---|---|---|---|
| Cl | Cl | CH₃ | Cl | CH₃ |  |
| Cl | CH₃ | CH₃ | | | |
| CH₃ | CH₃ | CH₃ | CH₃ | CH₃ |  |
| H | H | C₂H₅ | | | |
| H | Cl | C₂H₅ | H | Cl |  |
| H | CH₃ | C₂H₅ | | | |
| Cl | Cl | C₂H₅ | H | CH₃ |  |
| Cl | CH₃ | C₂H₅ | | | |
| CH₃ | CH₃ | C₂H₅ | Cl | Cl |  |
| H | H | n-C₃H₇ | | | |
| H | Cl | n-C₃H₇ | Cl | CH₃ |  |
| H | CH₃ | n-C₃H₇ | | | |
| Cl | Cl | n-C₃H₇ | H | H |  |
| Cl | CH₃ | n-C₃H₇ | | | |
| CH₃ | CH₃ | n-C₃H₇ | H | Cl |  |
| H | H | i-C₃H₇ | | | |
| H | Cl | i-C₃H₇ | H | CH₃ |  |
| H | CH₃ | i-C₃H₇ | | | |
| Cl | Cl | i-C₃H₇ | Cl | Cl |  |
| Cl | CH₃ | i-C₃H₇ | | | |
| CH₃ | CH₃ | i-C₃H₇ | Cl | CH₃ |  |
| H | H |  | CH₃ | CH₃ |  |
| H | Cl |  | H | H |  |
| H | CH₃ |  | H | Cl |  |
| H | CH₃ | tert. C₄H₉ | | | |

TABLE 1-continued

| R⁶ | R⁷ | R | R⁶ | R⁷ | R |
|---|---|---|---|---|---|
| H | CH₃ |  | CH₃ | CH₃ |  |
| Cl | Cl |  | H | H |  |
| Cl | CH₃ |  | H | Cl |  |
| CH₃ | CH₃ |  | H | CH₃ |  |
| H | H |  | Cl | Cl |  |
| H | Cl |  | Cl | CH₃ |  |
| H | CH₃ |  | CH₃ | CH₃ |  |
| Cl | Cl |  | H | H |  |
| Cl | CH₃ |  | H | Cl |  |
| CH₃ | CH₃ |  | H | CH₃ |  |
| H | H |  | Cl | Cl |  |
| H | Cl |  | Cl | CH₃ |  |
| H | CH₃ |  | CH₃ | CH₃ |  |
| Cl | Cl |  | H | H |  |
| Cl | CH₃ |  | H | Cl |  |
| Cl | Cl | tert. C₄H₉ | | | |
| Cl | CH₃ | tert. C₄H₉ | | | |
| H | CH₃ |  | H | Cl |  |
| Cl | Cl |  | H | CH₃ |  |
| Cl | CH₃ |  | Cl | Cl |  |
| CH₃ | CH₃ |  | Cl | CH₃ |  |

TABLE 1-continued

| R⁶ | R⁷ | R | R⁶ | R⁷ | R |
|---|---|---|---|---|---|
| H | H | 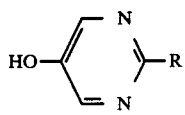—Cl | CH₃ | CH₃ | —⟨◯⟩—Cl |
| CH₃ | CH₃ | tert. C₄H₉ | | | |

The anilines of the formula (II) which are to be used as starting materials are new. The new compounds of the formula (II) are prepared by known processes, by reacting 5-hydroxypyrimidines of the formula (VI)

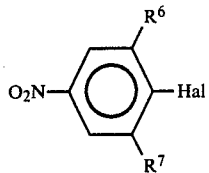

(VI)

in which R has the meaning given above, if appropriate in the form of the alkali metal, alkaline earth metal or ammonium salts, with compounds of the formula (VII)

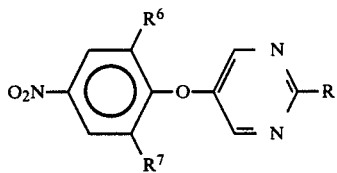

(VII)

in which
R⁶ and R⁷ have the meanings given above and
Hal represents halogen, in particular chlorine or bromine,
if appropriate in the presence of diluents, such as, for example, dimethylsulphoxide, and, if appropriate, in the presence of acid acceptors, such as, for example, potassium carbonate, potassium hydroxide or sodium hydroxide, at temperatures between 50° C. and 200° C., and reducing the new compounds obtained in this manner, of the formula (VIII)

$$O_2N-\underset{R^7}{\underset{|}{\overset{R^6}{\overset{|}{\bigcirc}}}}-O-\overset{N}{\underset{N}{\diagdown}}-R$$

(VIII)

in which R, R⁶ and R⁷ have the meanings given above, by customary methods, for example by reduction in an acidic medium with reducing agents, such as tin(II) chloride and hydrochloric acid, if appropriate in the presence of solvents, such as ethanol, at temperatures between −10° C. and +100° C., to give the corresponding new anilines of the formula (II) (see preparation examples).

The compounds of the formula (VI) are known and can be prepared by processes and methods known from the literature (see, for example, DE No. 2,634,262, DE No. 2,706,127 and DE No. 2,835,492).

The compounds of the formula (VII) are generally known compounds of organic chemistry.

The compounds of the formula (VIII) are new, and can be prepared by the process given above. The corresponding nitro derivatives of the compounds of the formula (II) in Table 1 may be mentioned as examples of the compounds of the formula (VIII).

The following may be mentioned as examples of the compounds of the formula (III): 2-fluoro-, 2-chloro-, 2-bromo-, 2-iodo-, 2-nitro-, 2-methyl-, 2-methylthio-, 2,4-dichloro-, 2,4-difluoro-, 2,4-dibromo-, 2,4-dimethyl-, 2-chloro-4-fluoro-, 4-chloro-2-fluoro-, 3-chloro-4-fluoro-, 3,4-dichloro-, 4-chloro-, 4-fluoro-, 4-bromo-, 2-chloro-5-fluoro-, 2-bromo-4-fluoro-, 2,5-dichloro-, 2,5-difluoro-, 5-chloro-2-fluoro-, 2,6-difluoro-, 2,6-dichloro-, 2,6-dibromo-, 2-chloro-6-fluoro-, 2-bromo-6-fluoro-, 2-methyl-6-fluoro- and 2-methylthio-6-fluoro-benzoyl isocyanate and -benzoyl iso-thiocyanate.

The benzoyl iso(thio)cyanates of the formula (III) are known.

Formula (IV) gives a definition of the pyrimidinyl-oxy-phenyl iso(thio)cyanates to be used for process variant (b).

The pyrimidinyloxy-phenyl iso(thio)cyanates of the formula (IV) are new. They can be prepared from the corresponding new substituted anilines of the formula (II) by generally customary methods (see, for example EP No. 0,057,888).

The following may be mentioned as examples of the starting compounds of the formula (V): 2-fluoro-, 2-chloro-, 2-bromo-, 2-iodo-, 2-nitro-, 2-methyl-, 2-methylthio-, 2,4-dichloro-, 2,4-difluoro-, 2,4-dibromo-, 2,4-dimethyl-, 2-chloro-4-fluoro-, 4-chloro-2-fluoro-, 3-chloro-4-fluoro-, 3,4-dichloro-, 4-chloro-, 4-bromo-, 4-fluoro-, 2-chloro-5-fluoro-, 2-bromo-4-fluoro-, 2,4-dichloro-, 2,5-difluoro-, 5-chloro-2-fluoro-, 2,6-difluoro-, 2,6-dichloro-, 2,6-dibromo-, 2-chloro-6-fluoro-, 2-bromo-6-fluoro-, 2-methyl-6-fluoro- and 2-methylthio-6-fluoro-benzoic acid amide.

Compounds of the formula (V) are known and can be obtained by generally known methods and processes (see, for example, Z.Obsc.Chim. 11 (1941) 243; C.A. 1941, 7965).

Virtually all inert organic solvents are suitable diluents for the process variants (a) and (b). These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and ethyl isobutyl ketone, esters, such as methyl acetate and ethyl acetate, nitriles, such as, for example, acetonitrile and propionitrile, amides, such as, for example, dimethylacetamide and N-methyl-pyrrolidone, and tetramethylenesulphone.

Preferred catalysts for the reaction according to process variant (b) are tertiary amines, such as triethylamine and 1,4-diazabicyclo[2.2.2]octane, and organic tin compounds, such as, for example, dibutyl-tin dilaurate.

The reaction temperature can be varied within a relatively wide range. In general, process variant (a) is carried out at between 20° and 180° C., preferably between 60° and 120° C., and process variant (b) is carried out at between 20° and 200° C., preferably between 60° and 190° C. The process variants according to the invention are carried out in general under atmospheric pressure.

For carrying out the process variants (a) and (b) according to the invention, the starting materials are usually employed in about equimolar amounts. An excess of one or the other of the reactants has no substantial advantages.

The reaction products are worked up by customary methods, for example by filtering off the precipitated product under suction or by extracting undesired by-products from the reaction mixture. They are characterized by their melting points.

The preparation of the compounds of the formula (I) is preferably carried out using process variant (a).

In addition to relating to the compounds of the formula (I), the present invention also relates to their preparation and use, as well as to the intermediate products of the formula (II), (IV) and (VIII), which can be summarized by the formula (IX):

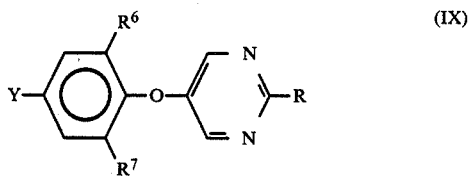

in which
R represents hydrogen, alkyl, cycloalkyl, halogenoalkyl or optionally substituted aryl,
$R^6$ and $R^7$ are identical or different and represent hydrogen, halogen or alkyl and
Y represents $NH_2$, $NO_2$ or NCX (preferably $NH_2$), wherein X denotes oxygen or sulphur.

The active compounds are well tolerated by plants, have a favorable level of toxicity to warm-blooded animals, and are suitable for combating animal pests, especially insects, arachnida and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus*, *Armadillidium vulgare* and *Porcellio scaber*. From the order of the Diplopoda, for example, *Blaniulus guttulatus*. From the order of the Chilopoda, for example, *Geophilus carpophagus* and *Scutigera* spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis*, *Periplaneta americana*, *Leucophaea maderae*, *Blattella germanica*, *Acheta domesticus*, Gryllotalpa spp., *Locusta migratori migratorioides*, *Melanoplus differentialis* and *Schistocerca gregaria*. From the order of the Dermaptera, for example, *Forficula auricularia*. From the order of the Isoptera, for example, Reticulitermes spp.. From the order of the Anoplura, for example, *Phylloxera vastatrix*, Pemphigus spp., *Pediculus humanus corporis*, Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius*, *Piesma quadrata*, *Cimex lectularius*, *Rhodnius prolixus* and Triatoma spp. From the order of the Homoptera, for example, *Aleurodes brassicae*, *Bemisia tabaci*, *Trialeurodes vaporariorum*, *Aphis gossypii*, *Brevicoryne brassicae*, *Cryptomyzüs ribis*, *Doralis fabae*, *Doralis pomi*, *Eriosoma lanigerum*, *Hyalopterus arundinis*, *Macrosiphum avenae*, Myzus spp., *Phorodon humuli*, *Rhopalosiphum padi*, Empoasca spp., *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, Pseudococcus spp. and Psylla spp. From the order of the Lepidoptera, for example, *Pectinophora gossypiella*, *Bupalus piniarius*, *Cheimatobia brumata*, *Lithiocolletis blancardella*, *Hyponomeuta padella*, *Plutella maculipennis*, *Malacosoma neustria*, *Euproctis chrysorrhoea*, Lymantria spp. *Bucculatrix thurberiella*, *Phyllocnistis citrella*, Agrotis spp., Euxoa spp., Feltia spp., *Earias insulana*, Heliothis spp., *Laphygma exigua*, *Mamestra brassicae*, *Panolis flammea*, *Prodenia litura*, Spodoptera spp., *Trichoplusia ni*, *Carpocapsa pomonella*, Pieris spp., Chilo spp., *Pyrausta nubilalis*, *Ephestia kuehniella*, *Galleria mellonella*, *Tineola bisselliella*, *Tinea pellionella*, *Hofmannophila pseudospretella*, *Cacoecia podana*, *Capua reticulana*, *Choristoneura fumiferana*, *Clysia ambiguella*, *Homona magnanima* and *Tortrix viridana*. From the order of the Coleoptera, for example, *Anobium punctatum*, *Rhizopertha dominica*, *Bruchidius obtectus*, *Acanthoscelides obtectus*, *Hylotrupes bajulus*, *Agelastica alni*, *Leptinotarsa decemlineata*, *Phaedon cochleariae*, Diabrotica spp., *Psylliodes chrysocephala*, *Epilachna varivestis*, Atomaria spp., *Oryzaephilus surinamensis*, Anthonomus spp., Sitophilus spp., *Otiorrhynchus sulcatus*, *Cosmopolites sordidus*, *Ceuthorrhynchus assimilis*, *Hypera postica*, Dermestes spp., Trogoderma spp., Anthrenus spp., Attagenus spp., Lyctus spp., *Meligethes aeneus*, Ptinus spp., *Niptus hololeucus*, *Gibbium psylloides*, Tribolium spp., *Tenebrio molitor*, Agriotes spp., Conoderus spp., *Melolontha melolontha*, *Amphimallon solstitialis* and *Costelytra zealandica*. From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus*, *Oscinella frit*, Phorbia spp., *Pegomyia hyoscyami*, *Ceratitis capitata*, *Dacus oleae* and *Tipula paludosa*.

From the order of the Siphonaptera, for example, *Xenopsylla cheopis* and Ceratophyllus spp.. From the order of the Arachnida, for example, *Scorpio maurus* and *Latrodectus mactans*.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants such as halogenated hydrocarbons as well as butane, propane, nitrogen and carbon dioxide; as solid carriers there are suitable: for example ground natural minerals, such as kaolins, clays, talc, chalk, quartz, attapulgite, montmorrillonite or diatomaceous earth, and ground synthetic minerals, such as highly dispersed silicic acid, alumina and silicates; as solid carriers for granules there are suitable: for example crushed and fractionated rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphate, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1%.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating ectoparasites and endoparasites in the field of animal husbandry and livestock breeding, it being possible to achieve better results, for example higher milk yields, higher weight, finer animal skin, longer life span, etc., by combating the pests.

The active compounds according to the invention are used in a known manner in these fields, such as by external application, for example in the form of dipping, spraying, pouring on and spotting on, and dusting, and by oral administration, for example via the feed or drinking water, for example in the form of tablets, capsules, drinks and granules.

The preparation examples which follow are intended to illustrate the preparation of the new compounds of the formula (I):

EXAMPLE 1

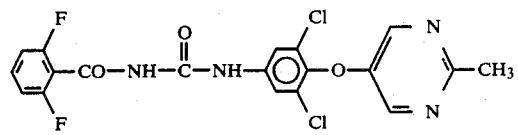

(Process variant a)

2.75 g (0.015 mole) of 2,6-difluorobenzoyl isocyanate in 10 ml of toluene are added dropwise to a solution of 4.05 g (0.015 mole) of 3,5-dichloro-4-(2-methylpyrimidin-5-yl-oxy)-aniline in 60 ml of dry toluene at 60° C. The mixture is then stirred for one hour at 80° C. After the mixture has been cooled to 20° C., the product is filtered off under suction and dried.

6.0 g (99.5% of theory) of N-[3,5-dichloro-4-(2-methyl-pyrimidin-5-yl-oxy)-phenyl]-N'-(2,6-difluoro-benzoyl)-urea of melting point m.p.: 263° C. are obtained.

EXAMPLE 2

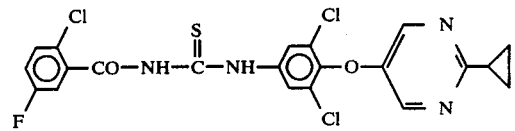

(Process variant b)

A solution of 21.6 g (0.01 mole) of 2-chloro-5-fluorobenzoyl isothiocyanate in 10 ml of toluene is added dropwise to a solution of 2.96 g (0.01 mole) of 3,5-dichloro-4-(2-cyclopropyl-pyrimidin-5-yl-oxy)-aniline in 50 ml of dry toluene at 60° C. The mixture is stirred for 30 minutes at 80° C. and is then cooled to 20° C. By adding petroleum ether, the reaction product is precipitated. It is then filtered off under suction and dried.

5.0 g (97.5% of theory) of N-[3,5-dichloro-4-(2-cyclopropyl-pyrimidin-5-yl-oxy)-phenyl]-N'-(3,5-dichlorobenzoyl)-urea of melting point m.p.: 176° C. are obtained.

The compounds of the formula (I) which are listed in Table 2 below can be prepared analogously to Example 1 and 2:

TABLE 2

$$\text{R}^2, \text{R}^1, \text{R}^3, \text{R}^4, \text{R}^5 \text{ substituted phenyl} - \text{CO}-\text{NH}-\text{CX}-\text{NH}- \text{R}^6, \text{R}^7 \text{ substituted phenyl with } -\text{CH}=\text{N}-\text{C(R)}=\text{N}- \text{ ring}$$ (I)

| Example No. | $R^1$ | $R^2$ | $R^3$ | $R^4$ | $R^5$ | $R^6$ | $R^7$ | R | X | m.p./°C. |
|---|---|---|---|---|---|---|---|---|---|---|
| 3 | H | Cl | F | H | H | Cl | Cl | $CH_3$ | O | 224 |
| 4 | F | H | Cl | H | H | Cl | Cl | $CH_3$ | O | 258 |
| 5 | F | H | H | H | F | H | H | $CH_3$ | O | 215 |
| 6 | Cl | H | H | H | F | H | H | $CH_3$ | O | 200 |
| 7 | Cl | H | H | H | F | Cl | Cl | $CH_3$ | O | 218 |
| 8 | Cl | H | H | H | H | Cl | Cl | cyclopropyl | O | 193 |
| 9 | F | H | H | H | F | Cl | Cl | cyclopropyl | O | 189 |
| 10 | Cl | H | H | H | F | Cl | Cl | cyclopropyl | O | 222 |
| 11 | I | H | H | H | H | Cl | Cl | cyclopropyl | O | 202 |
| 12 | F | H | H | H | F | H | H | cyclopropyl | O | 202 |
| 13 | Cl | H | H | H | Cl | H | H | cyclopropyl | O | 199 |
| 14 | Br | H | H | H | H | H | H | cyclopropyl | O | 173 |
| 15 | Cl | H | F | H | H | Cl | Cl | cyclopropyl | O | 220 |
| 16 | Cl | H | H | F | H | Cl | Cl | cyclopropyl | O | 197 |
| 17 | Br | H | H | H | H | Cl | Cl | cyclopropyl | O | 195 |
| 18 | $NO_2$ | H | H | H | H | Cl | Cl | cyclopropyl | O | 218 |
| 19 | $CH_3$ | H | H | H | H | Cl | Cl | cyclopropyl | O | 210 |
| 20 | F | H | H | H | F | Cl | Cl | cyclopropyl | S | 224 |
| 21 | Br | H | H | H | H | Cl | Cl | cyclopropyl | S | 191 |
| 22 | H | Cl | Cl | H | H | Cl | Cl | cyclopropyl | O | 234 |

TABLE 2-continued (I)

$$R^2, R^1, R^3, R^4, R^5 - \text{benzene} - CO-NH-CX-NH - \text{benzene}(R^6, R^7) - \text{pyrimidine} - R$$

| Example No. | R¹ | R² | R³ | R⁴ | R⁵ | R⁶ | R⁷ | R | X | m.p./°C |
|---|---|---|---|---|---|---|---|---|---|---|
| 23 | SCH₃ | H | H | H | H | Cl | Cl | cyclopropyl | O | 184 |
| 24 | H | H | Cl | H | H | Cl | Cl | cyclopropyl | O | 268 |
| 25 | Cl | H | F | H | H | Cl | Cl | cyclopropyl | S | 190 |
| 26 | F | H | H | H | F | Cl | Cl | –C₆H₄–CF₃ | O | 193 |
| 27 | Cl | H | H | H | H | Cl | Cl | –C₆H₄–CF₃ | O | 202 (decomp.) |
| 28 | Cl | H | H | H | F | Cl | Cl | –C₆H₄–CF₃ | S | 217 (decomp.) |
| 29 | F | H | H | H | F | CH₃ | CH₃ | cyclopropyl | S | 206–207 |
| 30 | Cl | H | F | H | H | CH₃ | CH₃ | cyclopropyl | S | 177 |
| 31 | Br | H | H | H | H | CH₃ | CH₃ | cyclopropyl | S | 201 |
| 32 | CH₃ | H | H | H | H | CH₃ | CH₃ | cyclopropyl | O | 202 |
| 33 | Cl | H | H | H | H | CH₃ | CH₃ | cyclopropyl | O | 177 |
| 34 | F | H | H | H | F | CH₃ | CH₃ | cyclopropyl | O | 188 |
| 35 | Cl | H | H | H | F | CH₃ | CH₃ | cyclopropyl | O | 219 |
| 36 | Cl | H | H | H | Cl | CH₃ | CH₃ | cyclopropyl | O | 221–222 |
| 37 | Cl | H | H | H | H | Cl | Cl | –CH(CH₃)₂ | O | 187 |
| 38 | Cl | H | F | H | H | Cl | Cl | –CH(CH₃)₂ | O | 212–213 |

TABLE 2-continued

![Formula I structure with R1-R7 substituents, CO-NH-CX-NH linkage and pyrimidine ring]

(I)

| Example No. | R¹ | R² | R³ | R⁴ | R⁵ | R⁶ | R⁷ | R | X | m.p./°C. |
|---|---|---|---|---|---|---|---|---|---|---|
| 39 | F | H | H | H | F | Cl | Cl | —CH(CH₃)₂ | O | 200 |
| 40 | F | H | H | H | F | Cl | Cl | —CH(CH₃)₂ | S | 177–179 |
| 41 | F | H | H | H | F | Cl | Cl | —C(CH₃)₃ | O | 193 |
| 42 | Cl | H | F | H | H | CH₃ | CH₃ | —CH(CH₃)₂ | O | 171 |

STARTING MATERIALS OF THE FORMULA (II)

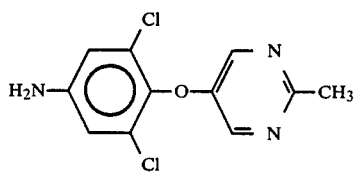

(II-1)

A solution of 101 g of tin(II) chloride dihydrate in 190 ml of concentrated hydrochloric acid is added dropwise to a suspension of 45 g (0.15 mole) of 3,5-dichloro-4-(2-methyl-pyrimidin-5-yl-oxy)-nitrobenzene and 225 ml of ethanol at 0° C. to 5° C. After the temperature has increased to 20° C., the mixture is stirred for 2 hours at 50° C. to 60° C. After the mixture has been cooled to 20° C., it is poured into ice-water, concentrated sodium hydroxide solution (200 g of sodium hydroxide and 300 ml of water) is added, the mixture is then extracted twice with ethylene chloride, and the extracts are washed three times with water and dried. After the solvent has been removed, 38.2 g (94% of theory) of 3,5-dichloro-4-(2-methyl-pyrimidin-5-yl-oxy)-aniline of melting point m.p.: 147° C. are obtained.

The other compounds of the formula (II) which are listed in Table 3 were prepared analogously to Example (II-1):

TABLE 3

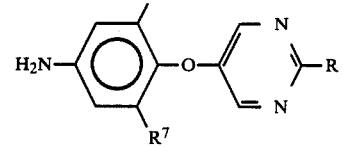

(II)

| Example No. | R⁶ | R⁷ | R | Melting point m.p./°C. |
|---|---|---|---|---|
| II-2 | H | H | CH₃ | 115 |
| II-3 | H | H | cyclopropyl | 97 |
| II-4 | Cl | Cl | cyclopropyl | 137 |
| II-5 | CH₃ | CH₃ | iso-C₃H₇ | 87 |
| II-6 | Cl | Cl | iso-C₃H₇ | 111 |
| II-7 | CH₃ | CH₃ | cyclopropyl | 137 |
| II-8 | Cl | Cl | iso-C₃H₇ | |
| II-9 | Cl | Cl | —C₆H₄—CF₃ | 98 |
| II-10 | Cl | Cl | tert.-C₄H₉ | 143–145 |

The reduction of the nitro compounds of the formula (VIII) to compounds of the formula (II) can also be carried out by means of hydrogen, with the aid of catalysts.

STARTING MATERIALS OF THE FORMULA (VIII)

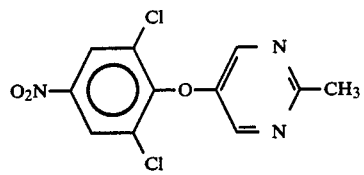

(VIII-1)

22 g (0.2 mole) of 2-methyl-5-hydroxy-pyrimidine are dissolved in 180 ml of dimethylsulphoxide, and a solution of 13 g of potassium hydroxide in 10 ml of water is added. The mixture is stirred for 30 minutes at 60° C. To remove the resulting water, about 40 ml are distilled off in vacuo. A solution of 45.4 g (0.2 mole) of 3,4,5-trichloro-nitrobenzene in 80 ml of dimethylsulphoxide is added to the residue, and the mixture is stirred for 4 hours at 80° C. to 100° C. and then cooled to 20° C. After the solid reaction product has been filtered off under suction, it is washed several times with water and finally recrystallised from aqueous methanol.

37.3 g (62% of theory) of 3,5-dichloro-4-(2-methyl-pyrimidin-5-yl-oxy)-nitrobenzene of melting point m.p.: 109° C. are obtained.

The other compounds of the formula (VIII) which are listed in Table 4 are prepared analogously to Example (VIII-1):

TABLE 4

(VIII)

| Example No. | $R^6$ | $R^7$ | R | Melting point m.p./°C. or refractive index $n_D^{20}$ |
|---|---|---|---|---|
| VIII-2 | H | H | $CH_3$ | 110 |
| VIII-3 | H | H | cyclopropyl | 81 |
| VIII-4 | Cl | Cl | cyclopropyl | 107 |
| VIII-5 | $CH_3$ | $CH_3$ | iso-$C_3H_7$ | 101 |
| VIII-6 | Cl | Cl | iso-$C_3H_7$ | $n_D^{20}$: 1.5915 |
| VIII-7 | $CH_3$ | $CH_3$ | cyclopropyl | 135 |
| VIII-8 | Cl | Cl | iso-$C_3H_7$ | |
| VIII-9 | Cl | Cl | phenyl-$CF_3$ | 131 |
| VIII-10 | Cl | Cl | tert.-$C_4H_9$ | viscous oil |

The examples which follow are intended to illustrate the biological activity of the new compounds:

EXAMPLE A

Plutella test

Solvent: 15 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*), as long as the leaves are still moist.

After the specified periods of time, the destruction in % is determined. 100% means that all the caterpillars have been killed; 0% means that none of the caterpillars have been killed.

In this test, for example, the compounds of Preparation Examples (1), (8), (9), (10), (12), (17), (20), and (21) show a degree of destruction of 100% after 7 days, for example at an active compound concentration of 0.001%.

EXAMPLE B

Test with *Lucilia cuprina* resistant larvae

Emulsifier:
  35 parts by weight of ethylene glycol monomethyl ether
  35 parts by weight of nonylphenol polyglycol ether To produce a suitable preparation of active compound, three parts by weight of active compound are mixed with seven parts by weight of the abovementioned mixture and the concentrate thus obtained is diluted with water to the particular desired concentration.

About 20 *Lucilia cuprina* res. larvae are introduced into a test tube which contains about 1 cm³ of horse muscle and 0.5 ml of the preparation of active compound. After 24 hours, the degree of destruction is determined.

In a test, for example with an active compound concentration of 1,000 ppm, for example the compound of preparation example (7) showed a destruction of 100%.

It is understood that the specification and examples are illustrative but not limitative of the present invention and that other embodiments within the spirit and scope of the invention will suggest themselves to those skilled in the art.

We claim:
1. A 3-(pyrimidin-5-yl-oxy-phenyl)-1-benzoyl-(thio)-urea of the formula

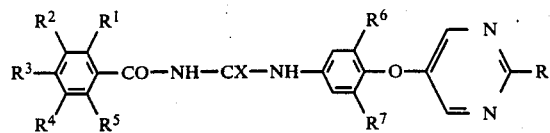

in which
  R represents hydrogen, $C_1$–$C_6$-alkyl, $C_3$–$C_6$-cycloalkyl, halogeno-$C_1$–$C_6$-alkyl, phenyl or a phenyl radical which is substituted by halogen, $C_1$–$C_4$-alkyl, $C_1$–$C_4$-alkoxy, $C_1$–$C_4$-alkylthio, halogeno-$C_1$–$C_4$-alkyl, halogeno-$C_1$–$C_4$-alkoxy and/or halogeno-$C_1$–$C_4$-alkylthio, $R^1$ represents hydrogen, nitro, halogen, $C_1$–$C_4$-alkyl or $C_1$–$C_4$-alkylthio, $R^2$, $R^3$, $R^4$ and $R^5$ are identical or different and represent hydrogen or halogen, and $R^6$ and $R^7$ are identical or different and represent hydrogen, halogen or $C_1$–$C_4$-alkyl, and X represents oxygen or sulphur.

2. A compound according to claim 1, in which

R represents hydrogen, $C_1$–$C_4$-alkyl, $C_3$–$C_6$-cycloalkyl, halogeno-$C_1$–$C_4$-alkyl, phenyl or phenyl which is substituted by $C_1$–$C_2$-alkyl, $C_1$–$C_2$-alkoxy, $C_1$–$C_2$-alkylthio, halogeno-$C_1$–$C_2$-alkyl, halogeno-$C_1$–$C_2$-alkoxy, halogeno-$C_1$–$C_2$-alkylthio, fluorine, chlorine and/or bromine, $R^1$ represents hydrogen, fluorine, chlorine, bromine, iodine, nitro, $C_1$–$C_4$-alkyl or $C_1$–$C_4$-alkylthio, $R^2$, $R^3$, $R^4$ and $R^5$ are identical or different and represent hydrogen, fluorine, chlorine or bromine, and $R^6$ and $R^7$ are identical or different and represent hydrogen, fluorine, chlorine, bromine or $C_1$–$C_4$-alkyl.

3. A compound according to claim 1, in which

R represents hydrogen, methyl, ethyl, n-propyl, i-propyl, n-butyl, sec.-butyl, i-butyl, ter.-butyl, cyclopropyl, cyclohexyl, or phenyl which is optionally monosubstituted to trisubstituted by methyl, ethyl, trifluoromethyl, trifluoromethoxy, trifluoromethylthio, fluorine, chlorine and/or bromine, $R^1$ represents fluorine, chlorine, bromine or iodine, $R^2$, $R^3$, $R^4$ and $R^5$ are identical or different and represent hydrogen, fluorine, chlorine or bromine, and $R^6$ and $R^7$ are identical or different and represent hydrogen, chlorine or methyl.

4. A compound according to claim 1, wherein such compound is N-[3,5-dichloro-4-(2-methyl-pyrimidin-5-yl-oxy)-phenyl]-N'-(2,6-difluorobenzoyl)-urea of the formula

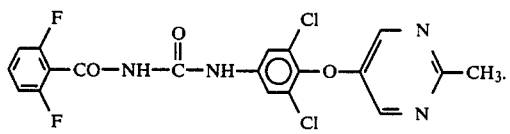

5. A compound according to claim 1, wherein such compound is N-[3,5-dichloro-4-(2-cyclopropyl-pyrimidin-5-yl-oxy)-phenyl]-N'-(2,6-difluorobenzoyl)-urea of the formula

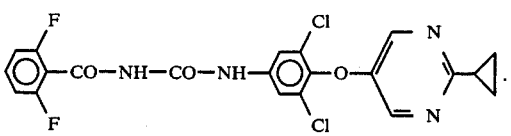

6. A compound according to claim 1, wherein such compound is N-[3,5-dichloro-4-(2-cyclopropyl-pyrimidin-5-yl-oxy)-phenyl]-N'-(2-chloro-6-fluoro-benzoyl)-urea of the formula

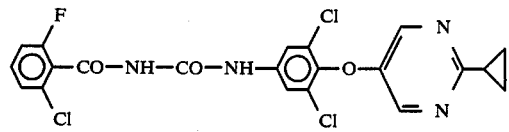

7. A compound according to claim 1, wherein such compound is N-[3,5-dichloro-4-(2-cyclopropyl-pyrimidin-5-yl-oxy)-phenyl]-N'-(2-bromo-benzoyl)-urea of the formula

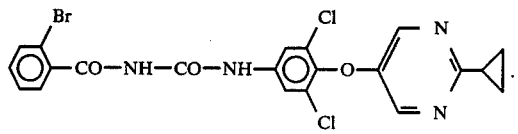

8. A compound according to claim 1, wherein such compound is N-[3,5-dichloro-4-(2-cyclopropyl-pyrimidin-5-yl-oxy)-phenyl]-N'-(2-bromo-benzoyl)-thiourea of the formula

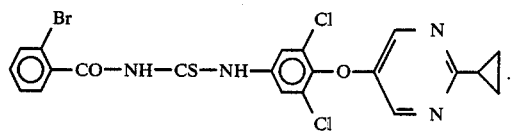

9. An arthropodicidal composition comprising an arthropodicidally effective amount of a compound according to claim 1 in admixture with a diluent.

10. A method of combatting arthropods which comprises administering to such arthropods or to an arthropod habitat an arthropodicidally effective amount of a compound according to claim 1.

11. The method according to claim 10, wherein such compound is
N-[3,5-dichloro-4-(2-methyl-pyrimidin-5-yl-oxy)-phenyl]-N'-(2,6-difluorobenzoyl)-urea,
N-[3,5-dichloro-4-(2-cyclopropyl-pyrimidin-5-yl-oxy)-phenyl]-N'-(2,6-difluorobenzoyl)-urea,
N-[3,5-dichloro-4-(2-cyclopropyl-pyrimidin-5-yl-oxy)-phenyl]-N'-(2-chloro-6-fluoro-benzoyl)-urea,
N-[3,5-dichloro-4-(2-cyclopropyl-pyrimidin-5-yl-oxy)-phenyl]-N'-(2-bromo-benzoyl)-urea or
N-[3,5-dichloro-4-(2-cyclopropyl-pyrimidin-5-yl-oxy)-phenyl]-N'-(2-bromo-benzoyl)-thiourea.

12. A compound of the formula

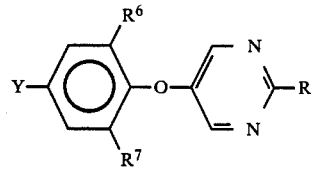

in which
R represents hydrogen, $C_1$–$C_6$-alkyl, $C_3$–$C_6$-cycloalkyl, halogeno-$C_1$–$C_6$-alkyl, phenyl or a phenyl radical which is substituted by halogen, $C_1$–$C_4$-alkyl, $C_1$–$C_4$-alkoxy, $C_1$–$C_4$-alkylthio, halogeno-$C_1$–$C_4$-alkyl, halogeno-$C_1$–$C_4$-alkoxy and/or halogeno-$C_1$–$C_4$-alkylthio, $R^6$ and $R^7$ are identical or different and represent hydrogen, halogen or $C_1$–$C_4$-alkyl, and Y represents $NO_2$, $NH_2$ or NCX, wherein X denotes oxygen or sulphur.

* * * * *